United States Patent
Pacella et al.

(12)
(10) Patent No.: US 6,186,149 B1
(45) Date of Patent: Feb. 13, 2001

(54) OCCLUDER DEVICE AND METHOD OF MAKING

(75) Inventors: John J. Pacella, Pittsburgh; Richard E. Clark, Sewickley, both of PA (US)

(73) Assignee: Allegheny-Singer Research Institute, Pittsburgh, PA (US)

( * ) Notice: Under 35 U.S.C. 154(b), the term of this patent shall be extended for 0 days.

(21) Appl. No.: 09/524,647

(22) Filed: Mar. 13, 2000

Related U.S. Application Data

(63) Continuation of application No. 08/228,150, filed on Apr. 15, 1994, now Pat. No. 6,045,496.

(51) Int. Cl.$^7$ .......................................... A61M 1/12

(52) U.S. Cl. ............................................ 128/898

(58) Field of Search .................. 623/3; 600/16, 600/17, 18; 128/686, 888, 899

(56) References Cited

U.S. PATENT DOCUMENTS

| | | | |
|---|---|---|---|
| 5,479,946 | * 1/1996 | Trumble | 128/899 |
| 5,826,584 | * 10/1998 | Schmitt | 128/898 |

* cited by examiner

Primary Examiner—Scott M. Getzow
(74) Attorney, Agent, or Firm—Ansel M. Schwartz

(57) ABSTRACT

The present invention pertains to a circulatory system, such as a circulatory assist system for a patient. The system comprises a blood pump having tubing fluidically communicating with a person's blood vessel. The blood pump can be, for instance, a centrifugal blood pump but is not limited thereto. The system also comprises an occluder device for controlling flow of the blood pump. The occluder device is in contact with the tubing of the blood pump. The occluder device can be incorporated into an anti-kink sheath over the outlet graft tubing of the blood pump. Preferably, the system comprises control means for actuating the occluder device when the blood pump malfunctions. In this manner, potentially fatal retrograde blood due to pump failure is automatically prevented. In a preferred embodiment, the occluder device comprises a cylindrical tube and a bladder mechanism connected to the inside surface of the tube. Type bladder mechanism preferably comprises a bladder and means for inflating the bladder. The inflating means preferably comprises a bladder pump having a tube in fluidic communication with the bladder. The bladder can be of a variety of constructions in the tube. The bladder can cover all or a portion of the inner surface of the tube. Also, two bladders can oppose each other, in a non-overlapping manner, within the tube. Alternatively, the bladder can cover the entire 360° of the inner surface. In this manner, as the bladder is inflated, the orifice closes with decreasing diameter, much like a natural biological valve. The occluder device could be rapidly inflated and deflated for applications as a valve either internally or externally. This would transform the normal steady flow output of a blood pump to a pulsatile output.

7 Claims, 5 Drawing Sheets

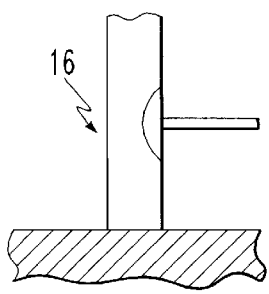
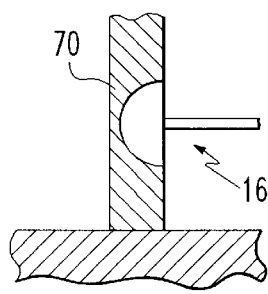
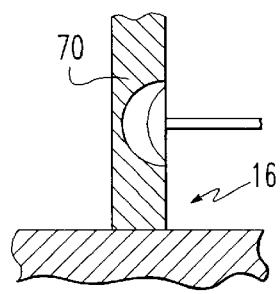
FIG.7a  FIG.7b  FIG.7c
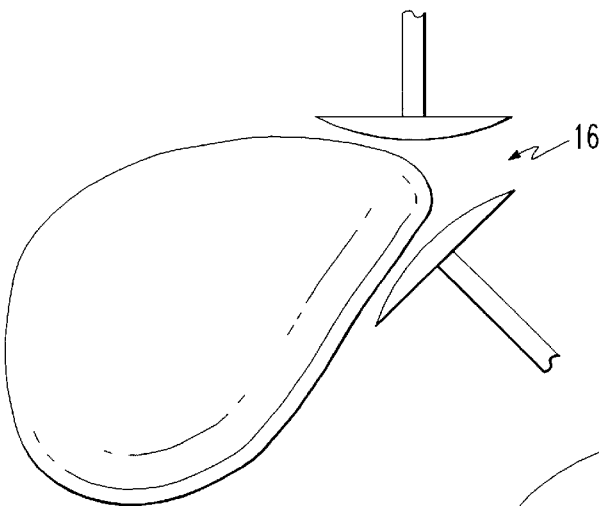
FIG.8a
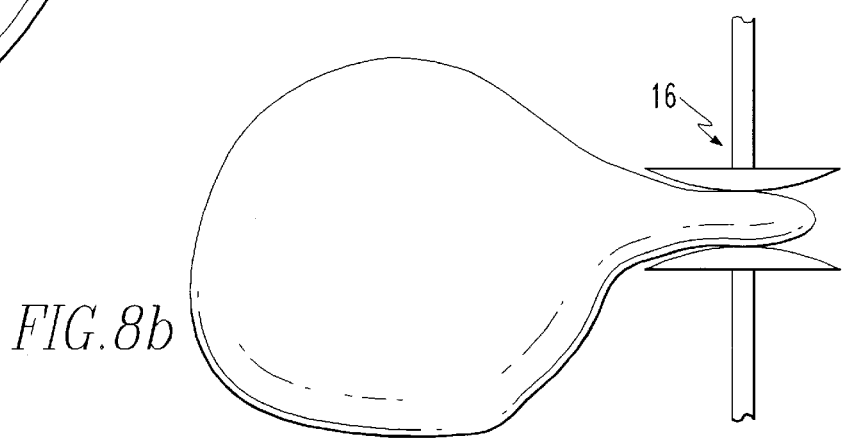
FIG.8b
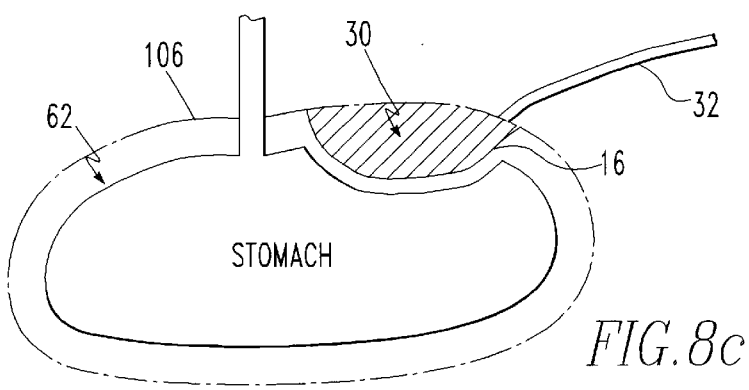
FIG.8c

OCCLUDER DEVICE AND METHOD OF MAKING

CROSS-REFERENCE

This is a continuation application of Ser. No. 08/228,150 filed Apr. 15, 1994, now U.S. Pat. No. 6,045,496.

This application is related to contemporaneously filed U.S. patent application Ser. No. 08/228,586, titled "Muscle Energy Converter", by Dennis R. Trumble, having attorney docket number AHS-5, incorporated by reference herein; and is related to contemporaneously filed U.S. patent application Ser. No. 08/228,433, titled "Blood Pump Device and Method of Producing", by John J. Pacella, Andrew H. Goldstein, Dennis R. Trumble, Richard E. Clark and Fred W. Moeller, incorporated by reference herein.

FIELD OF THE INVENTION

The present invention is related in general to medical devices. More specifically, the present invention is related to an occluder device and related systems and methods.

BACKGROUND OF THE INVENTION

It is known that in the event of blood pump motor failure, potentially fatal retrograde blood flow can occur between the descending aorta and the left atrium, resulting in immediate heart failure. The present invention can be used to prevent reverse flow through automatic occlusion of the pump outlet flow tube during and/or following pump failure.

Furthermore, the occluder device can function as an anti-kink sheath for the junction of the rigid outlet port of the blood pump housing and the flexible outlet flow tube. The anti-kink sheath eases the transition through its semi-flexible characteristics.

Prior art of vascular occluder includes U.S. Pat. No. 5,057,118, which describes a vessel occlusion device. The device has an adjustable metal clip consisting of a foam base. It supposedly results in little trauma to vessels. One problem is that it cannot be activated remotely.

U.S. Pat. No. 5,074,869 discloses a vascular occlusion device. This device comprises a pressure tube molded to a slender bladder. The bladder is wrapped around the vessel and secured with a suture. It is designed to work on small vessels in areas that are not easily accessible. There is no mention of artificial graft applications in ventricular assist devices or automatic applications.

U.S. Pat. No. 5,152,770 describes an implantable device for occluding a duct in the body of a living being. This device operates similarly to the previous system. It is wrapped and secured around a vessel and inflated. Again, no mention of artificial graft applications or automation is made.

U.S. Pat. No. 3,538,917 describes a balloon occlusion clip. This device comprises a rigid outer C-shell with a bladder molded to the inside of the shell. The device is put in place by spreading the C-shell and placing over the vessel.

None of the aforementioned patents are concerned with circulatory assist devices or the prevention of retrograde flow therethrough.

SUMMARY OF THE INVENTION

The present invention is a circulatory system, such as a circulatory assist system for a patient. The system comprises a blood pump having tubing fluidically communicating with a person's blood vessel. The blood pump can be, for instance, a centrifugal blood pump but is not limited thereto. The system also comprises an occluder device for controlling flow of the blood pump. The occluder device is in contact with the tubing of the blood pump. The occluder device can be incorporated into an anti-kink sheath over the outlet graft tubing of the blood pump. Preferably, the system comprises control means for actuating the occluder device when the blood pump malfunctions. In this manner, potentially fatal retrograde blood flow due to pump failure is automatically prevented.

In a preferred embodiment, the occluder device comprises a cylindrical tube and a bladder mechanism connected to the inside surface of the tube. The bladder mechanism preferably comprises a bladder and means for inflating the bladder. The inflating means communication with the bladder. Preferably, the bladder mechanism also comprises a pressure sensing means such as a hysteresis pressure switch. Preferably, the control means also comprises means for sensing blood pump failure.

The occluder device can be connected with the tubing of the blood pump either externally, or in-line. With the external construction, the tubing of the blood pump passes through the occluder tube. The tubing is unbroken and thus the blood never contacts the occluder device. The in-line construction comprises a connection between each end of the pump outlet tubing and the occluder tube. In this manner, blood flows through the occluder tube and contacts the bladder. Thus, with the in-line construction, it is absolutely critical that the blood contacting surface of the tube/bladder and the occluder tube/outlet tube interfaces be continuous to avoid surface anomalies and subsequent thrombus formation. That is, the presence of significant varying surface profiles, air bubbles, holes, or any other slight discontinuities at these areas can result in irregular blood flow patterns and eventual thrombosis. Another in-line arrangement could involve molding the bladders directly onto the inner wall of the pre-existing inlet tube of the blood pump. This method would eliminate the need to create interfaces between the occluder tube and the outlet tube. The inlet tube of the blood pump would serve as the occluder tube.

The bladder can be of a variety of constructions in the occluder tube. The bladder can cover all or a portion of the inner surface of the tube. Also, two bladders can oppose each other, in a non-overlapping manner within the tube. Alternatively, the bladder can cover the entire 360° of the inner surface and function as a ring bladder. In this manner, as the bladder is inflated, the orifice closes with decreasing diameter, much like a natural biological valve.

The occluder device could be rapidly inflated and deflated for applications as a valve in an internal configuration, with the bladders in direct contact with the blood stream. The device could be used in the same fashion externally, with the bladders directly opposing the outer wall of the outlet flow tube. In either case, the normal steady flow output of a blood pump (when heart completely dysfunctional) would be transformed to a pulsatile output.

The present invention also pertains to an occluder device exclusively. The occluder device comprises a tube having a closed annular cross section and an inflatable bladder mechanism connected to the inner surface of the tube. The unique closed annular shape of the tube provides a permanent frame and can be used as a flow channel, or as another example, as an anti-kink sheath for flexible tubing.

The present invention also pertains to a method of forming an occluder. The method comprises the step of disposing a mask material, such as gelatin, on an inner surface of a tube. Next, there is the step of applying a bladder material to the inner surface over the mask material. Then, there is the step of providing a hole through the tube under the mask material for inflating the bladder material. Preferably, after the providing step, there is the step of removing the mask material through the hole.

BRIEF DESCRIPTION OF THE DRAWINGS

In the accompanying drawings, the preferred embodiment of the invention and preferred methods of practicing the invention are illustrated in which:

FIGS. 7a–7c are schematic representations showing the occluder device used for molding a component.

FIGS. 8a–8c are schematic representations showing the occluder device squeezing the stomach.

DESCRIPTION OF THE PREFERRED EMBODIMENT

Figure 1:
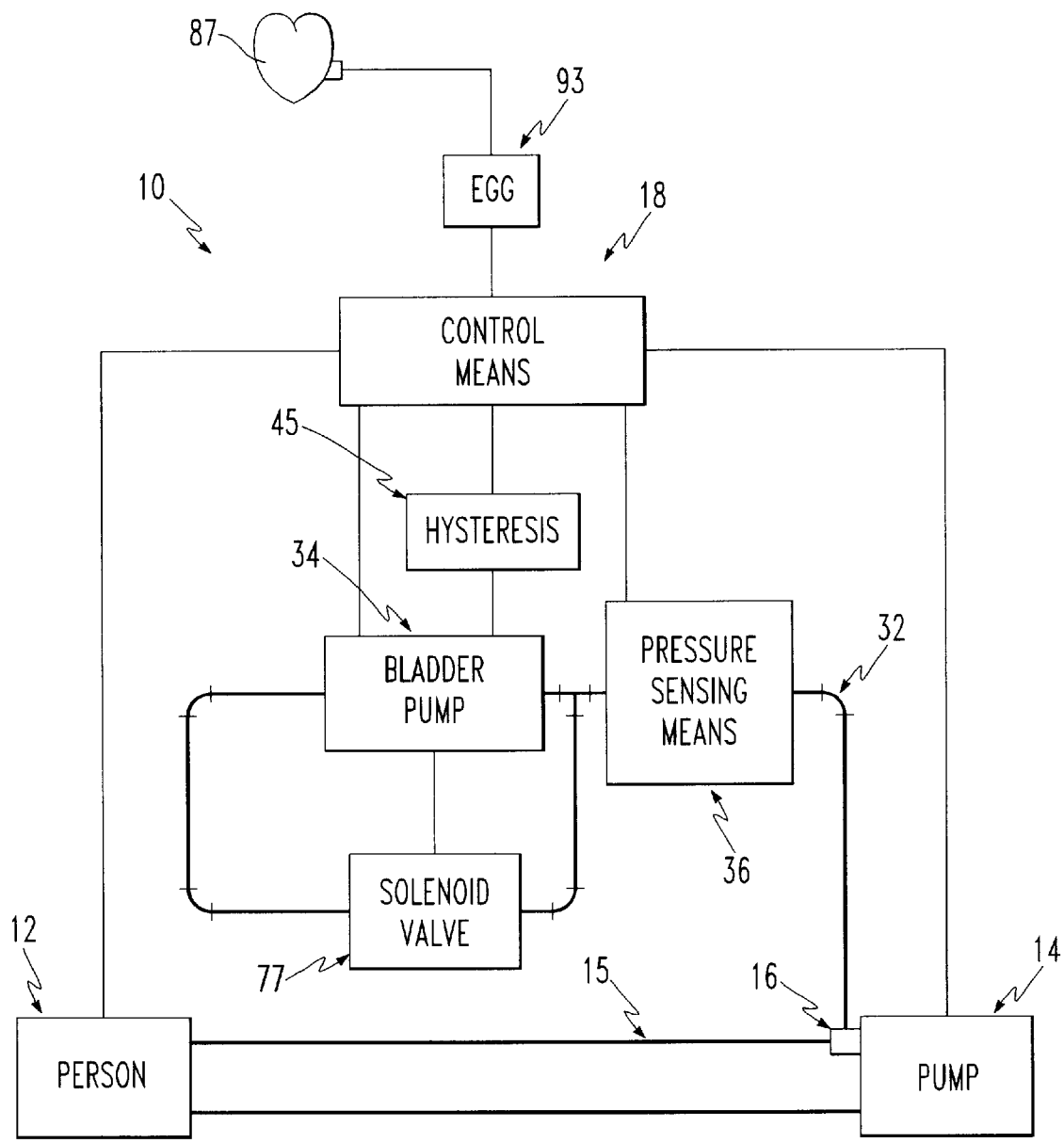
FIG. 1 is a schematic representation of the circulatory system with the occluder device.
Figure 2A:
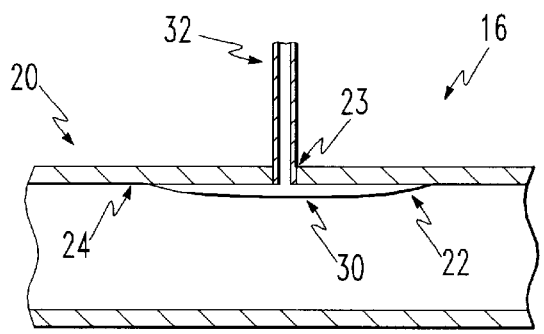
FIGS. 2a–2d are schematic representations showing cross sections through the occluder device.
Figure 2B:
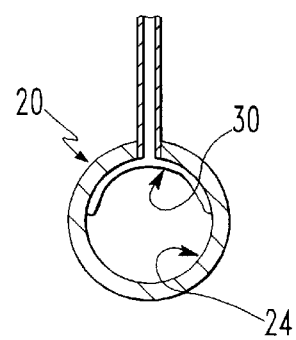
Figure 2C:
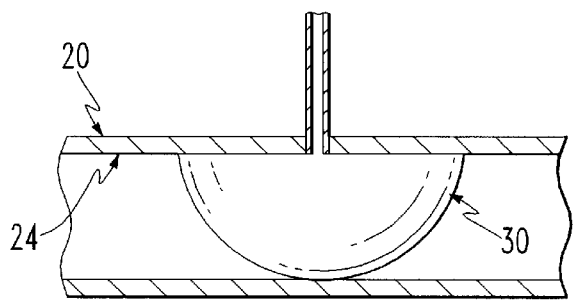
Figure 2D:
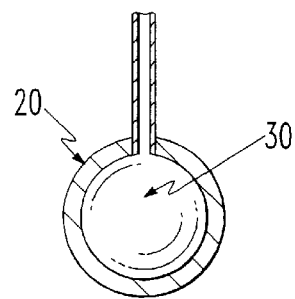

Referring now to the drawings wherein like reference numerals refer to similar or identical parts throughout the several views, and more specifically to FIG. 1 thereof, there is shown a circulatory system 10, such as a circulatory assist system for a patient 12. The system 10 comprises a blood pump 14 having tubing 15 fluidically communicating with a person's blood vessel. The blood pump 14 can be, for instance, a centrifugal blood pump but is not limited thereto. The system 10 also comprises an occluder device 16 for controlling flow of fluid by the blood pump 14. The occluder device 16 is in contact with the tubing 15 of the blood pump 14. The occluder device 16 can be incorporated into an anti-kink sheath over the outlet graft tubing 15 of the blood pump 14. Preferably, the system 10 comprises control means 18 for actuating the occluder device 16 when the blood pump 14 malfunctions. In this manner, potentially fatal retrograde blood flow due to pump failure is automatically prevented.

In a preferred embodiment and as best shown in FIGS. 2a–2d, the occluder device 16 comprises a cylindrical tube 20 and a bladder mechanism 22 connected to the inside surface 24 of the tube 20. The bladder mechanism 22 preferably comprises a bladder 30 and means for inflating the bladder 30. The inflating means preferably comprises a bladder pump 34 having a bladder tube 32 in fluidic communication with the bladder 30. A fluid, either liquid or gas, such as air, could be used for inflation of the bladder 30. Liquid is more likely to maintain pressure than gas. Gas will require more re-inflation because of its potential ability to diffuse through the bladder 30. Liquid for inflation could be stored internally and pumped through a small, implantable pump to the bladder 30 in the event of pump failure.

Figure 10:
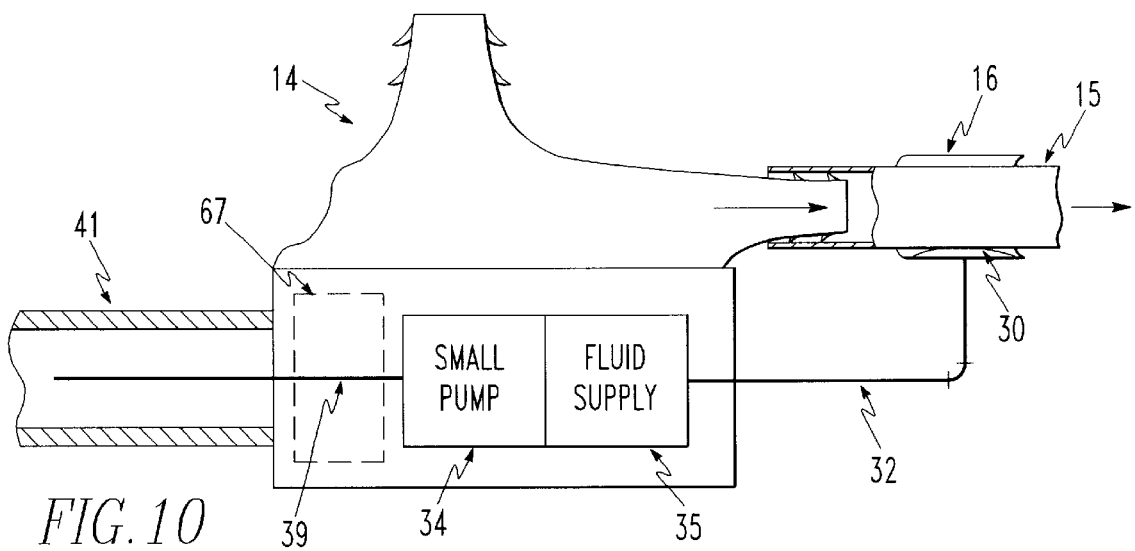
FIG. 10 is a schematic representation of the occluder in use as a safety occluder for a centrifugal blood pump.

Such an implantable pump 34 can be a small, implantable peristaltic pump which is readily available in the marketplace. One of these pumps could be used with a small container (5 mL volume) of liquid such as sterile $H_2O$ serving as the fluid supply 35. The bladder pump 34 and its fluid supply could be implanted near the blood pump 14. As shown in FIG. 10, the pump 34 and its supply 35 may attach to the lower housing/stator assembly of a centrifugal pump 14. The distance between the bladder pump's output and the occluding actuator 16 on the centrifugal pump outflow tube 15 should be minimized in order to reduce the work necessary to move fluid to and from the occluder bladder(s) 30. Also, by keeping this distance as small as possible, the length of tubing 15 in fluidic communication with the occluder bladder 30 will be minimized, thus limiting the quantity of implanted foreign material. In general, it is desirable to minimize the total amount of foreign implanted material for many reasons, including more stringent regulatory requirements from the FDA. The positive and negative leads 39 that deliver power to the bladder pump 34 could be incorporated with the cable 41 that carries current to the centrifugal pump 14.

For use as a blood contacting valve, however, liquid, not air, should be used to inflate the occluder bladder due to the risk of air emboli in the blood. Air in the bloodstream could result in immediate death. The liquid could be 0.9% saline solution, $D_5W$ sugar solution, sterile water, lipid solution, or any number of blood biocompatible liquids. Preferably, the bladder mechanism 22 also comprises a pressure sensing means 36 having a hysteresis pressure switch. This switch prevents bladder rupture due to over-inflation. Also, for sustained occlusion, it enables power to the bladder pump 34 when the bladder pressure decreases a certain percentage from a predetermined cut-off pressure.

Preferably, the control means 18 also comprises means for sensing blood pump 14 failure. The pump failure signal can be of any reliable type, including that corresponding to blood pump flow rate, blood pump motor current, blood pump speed, and blood pressure in either of the four chambers of the heart or the great vessels. Details of control means 18 for sensing pump failure and actuating an occluder is given in U.S. patent application Ser. No.08/228,433, titled "Blood Pump Device and Method of Producing" by John J. Pacella, Andrew H. Goldstein, Dennis R. Trumble, Richard E. Clark and Fred W. Moeller, having attorney docket number AHS-4, filed the same day as the present application, incorporated by reference herein.

In one embodiment, pump speed is used to actuate the occluder mechanism 22. This can be done by monitoring with stator Hall effect sensors 67 in stator of a conventional centrifugal pump to determine whether or not they are toggling between high and low as they should during proper pump impeller rotation. If the rotor-impeller assembly has stopped spinning, the Hall effect sensors 62 will no longer switch, and this can be used as the initiation signal for the occluder mechanism 22. Preferably, this is accomplished by incorporating a delay in occluder inflation to rule out spurious and/or transient signals. It must be ascertained that a no-spin condition of the pump 14 is stable and not transient.

In another embodiment, the control means 18 monitors current supplied to the blood pump stator and initiates occlusion when the current is zero (this indicates that the RPM=0). Two other methods that could be employed for safety occluder initiation are threshold speed and total power failure. Threshold speed would involve the controller determining pump speed and activating the occluder 16 if the speed falls below a critical RPM. That is, the blood pump RPM must be maintained above certain speeds in order to achieve forward flow since centrifugal pumps are sensitive to outlet pressure. It is possible to have retrograde flow through the blood pump 14 at a given RPM if the pressure on the outlet side of the pump generated by the intact heart is sufficient. The occluder 16 could then be activated should the speed fall below the threshold level. This critical speed will vary among patients. As an example, the range is 1500–2500 RPM in sheep with mean aortic pressures of 75–90 mmHg. Total power failure entails some type of complete interruption of the power being delivered to the blood pump stator. This could occur anywhere from the wall outlet to the internal circuitry of the controller.

The occluder bladder cut-off pressure can be programmable with a hysteresis switch 45 of the pressure sensing means and therefore can accommodate variations in occluder design and hydraulic requirements. Also, the activation of occluder 16 could be programmable. That is, the time and duration of the occlusion is regulated based on blood pump motor speed feedback. Depending on the size of the occluder bladder 30 and the pressure and flow that the occluder 30 must stop, accommodation for different bladder pressures may be necessary. This is accomplished by adjusting the hysteresis pressure switch's maximum cut-off pressure which can range from 8–16 psi. Hence, the switch 45 can be programmed to give the most adequate occlusion using only the minimum necessary pressure. Furthermore, the control means 18 may sense the occurrence of pump restart after an occlusion during temporary pump failure and therefore deactivate occluder power and bleed the bladder 30. This function serves as a valuable programmable function in the event of blood pump recovery from temporary failure.

The bladder pump 34 can be any compact reliable fluid pump such as a 20 psi miniature pneumatic diaphragm pump. Such a pump is manufactured in Germany by ASF, Inc. This pump draws approximately 2.3 Watts at continuous operation (240 mA, 9.5 Volts). At pressure regulated operation (pump turned on and off) the pump consumes very little power. A typical pressure in the bladder 30 required to cause total occlusion is 8 psi (ranges from 5–16 psi depending on hydraulics and bladder design). This pressure is regulated in the bladder 30 through the use of the pressure sensor means 36 which includes the hysteresis switch 45. The switch 45 remains closed until the bladder pressure is greater than 8 psi. At this point, the switch 45 opens and therefore interrupts power to the bladder pump 34. Once the bladder pressure drops 40% from the maximum value (at 5 psi), the switch 45 closes to enable power to the bladder pump 34. The bladder pump 34 then re-inflates the bladder 30 to 8 psi and the cycle repeats. In this way, bladder pressure is maintained between 5–8 psi at all times.

The pump 34 can be external or internal to a patient's body. When the pump 34 is external, pressure tubing 32 attached to the occluder 16 passes through an incision and out to the pump 34 With the bladder pump 34 arranged external to or outside of the body, the small size (approx ⅛ inch) of the pressure tubing will not add significantly to the risk of infection because larger tubes are already used for the pump lubricant and power cables. A triple lumen tube may be used to carry the blood pump lubricant, blood pump current, and either liquid or gas for bladder inflation. This would reduce the total surface area passing through the skin.

The bladder pump 34 may also be implanted with a blood pump 14, as shown in FIG. 10. Its location is dependent on the application. Within the body, the pressure tubing 32 is fastened between the occluder 16 and the blood pump 34. The chance of infection would be reduced if the bladder pump 34 and its supply 35 were positioned inside of the body. In this case, the small bladder pump 34 and its supply fluid reservoir 35 can be attached to the blood pump housing. The power cables 39 for the bladder pump 34 can be passed through the conduit 41 that holds the power cables for the blood pump 14.

Figure 4A:
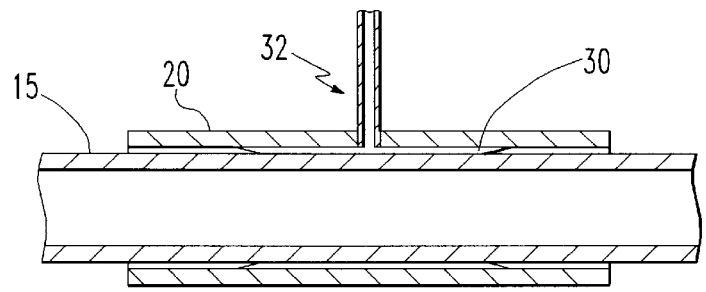
FIGS. 4a and 4b are schematic representations showing different embodiments of the occluder device attached to tubing.
Figure 4B:
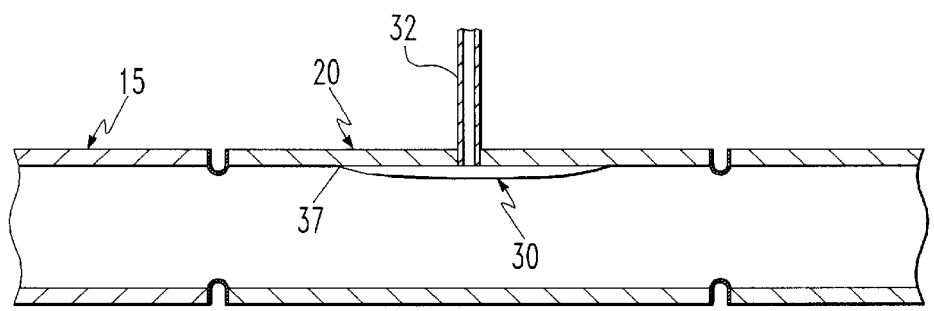

The occluder device 16 can be connected with the tubing 15 of the blood pump either externally thereto, as shown in FIG. 4a, or in-line as shown in FIG. 4b. With the external construction, the tubing 15 of the blood pump 14 passes through the tube 20. The tubing 15 is unbroken and thus the blood never contacts the occluder device 16. With the in-line construction, the tubing 15 is connected at each end of the tube 20. Blood flows through the tube 20 in contact with the bladder 30. Thus, with the in-line construction, it is absolutely critical that the blood contacting surface of the tube/bladder interface 37 be continuous to avoid clotting. As shown in FIG. 4b, with the in-line connection, the tubing 20 of the occluder is preferably molded directly with Gore-Tex® outlet graft tubing 15. Each junction is securely fastened (with sutures) and coated with, preferably, polyurethane to prevent clot formation.

Figure 3A:
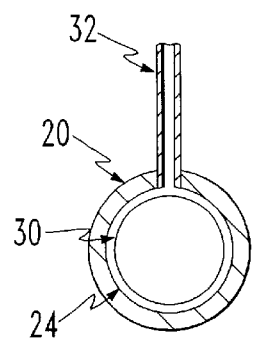
FIGS. 3a and 3b are schematic representations showing cross sections of the occluder device having a ring bladder.
Figure 3B:
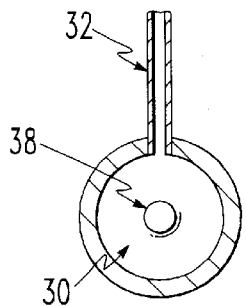

The bladder 30 can be of a variety of constructions in the tube 20. As shown in FIGS. 2a–2d, the bladder 30 can cover all or a portion of the inner surface of the tube 30. Also, two bladders can oppose each other, in a non-overlapping fashion within the tube 20. Alternatively, as shown in FIG. 3a, the bladder 30 can cover the entire 360° of the inner surface 24. In this manner, as illustrated in FIG. 3b, as the bladder 30 is inflated, the orifice 38 closes with decreasing diameter, much like a natural biological valve.

The occluder device 16 could be rapidly inflated and deflated for applications as a valve either in an in-line configuration or with the bladders opposing the external surface of the outlet flow tube. This would transform the normal steady flow output of a blood pump (when heart completely dysfunctional) to a pulsatile output. This could also be accomplished by rapidly varying pump RPM. Even with a partially functional heart, the degree of pulsatility in the pump output will be enhanced.

The bladder pump 34 could be inflated and deflated rapidly to cause rapid compression and decompression of the outlet pump graft tubing 15. For this embodiment, the blood pump tubing 15 needs to be molded with materials that can handle cyclic stress generated during bladder inflation. The tubing 15 could be comprised of Gore-tex®—polyurethane—Gore-tex® segments connected in series.

This occluder device 16 could also be used as a pressure controller and flow regulator for a blood pump 14. Simply by increasing bladder pressure, either used in-line or with the bladders opposing the external surface of the outlet flow tube, the systemic vascular resistance can be increased to decrease flow and pressure increase.

By employing a powerful vacuum in with the bladder pump 34 to deflate the bladder 30 or by furrowing out the inner wall 24 of the tube 20, it is possible to allow the bladder 30 to meet flush with the rest of the wall surface 24. As shown in FIG. 1, vacuum deflation could be accomplished by connecting the vacuum side of the bladder pump 34 to a solenoid valve 77 and using the solenoid valve switch 77 to allow rapid deflation of the bladder 30. The bladder 30 could be inflated on a one-time basis for safety occlusion or it could be rapidly inflated and vacuum deflated in synchrony with the ECG to provide pulsatile flow of the heart 87. This would supply a more physiologic flow pattern and allows the device to be used as a long-term circulatory assist tool.

In addition, it is possible to simulate the closing nature of an intact, biologic valve by fabricating a continuous ring bladder 30 on the inner surface 24 of the tube 20, as shown in FIGS. 3a and 3b. When this bladder 30 is inflated, the orifice 38 closes as a circle with decreasing radius. This closing pattern is more natural and simulates normal physiologic function more closely. Therefore, it may offer long-term advantage when compared to a bladder 30 on only a partial arc of the inner wall 24 of the tube 20.

The present invention also pertains to an occluder device 16. The occluder device 16 comprises a tube 20 having a closed annular cross section and an inflatable bladder mechanism 22 connected to the inner surface 24 of the tube 20. Previous conventional bladder occluders have an open C-shaped ring which must be tied closed after installation. The unique closed annular shape of the tube 20 is advantageous in many aspects. For instance, it provides a permanent frame and can be used as a flow channel, or as another example, as an anti-kink sheath for flexible tubing 15.

The present invention also pertains to a method of forming an occluder. The method comprises the step of disposing a mask material, such as gelatin, on an inner surface 24 of a tube 20. Next, there is the step of applying a bladder material 30 to the inner surface 24 over the mask material. Then, there is the step of providing a hole 23 through the tube 20 under the mask material for inflating the bladder material 30. Preferably, after the providing step, there is the step of removing the mask material through the hole 23.

The removing step can include the step of circulating a heated fluid through the hole 23 to dissolve the mask material. Preferably, after the circulating step, there is the step of attaching a tube 32 to the hole 23. Preferably, the applying step includes the step of pouring bladder material into the tube 20.

In a specific example of fabrication:

1. A PVC tube 20 (not necessarily PVC- other types of tubing are possible-see cover letter) is marked to define the outline of the bladder.
2. Gelatin is mixed in a four times normal concentration and stained with 3 drops of green food coloring.
3. The gelatin mixture is then applied to the inner surface 24 of the tube 20 within the outlined boundary with a cotton swab. It is applied in several coats with 2–3 minutes drying time between each coat. Also, the tube is spun axially to provide a smooth gelatin coating.
4. After the gelatin is dry (10–15 minutes after the initial coating), the tube 20 is held vertically in a 50 mL beaker. Polyurethane mixture is poured into the tube up to ⅛ inch before the top edge. The tube 20 is then lifted out of the beaker to simulate a dipping motion. The tube 20 is again axially spun and 20–30 minutes are allowed between dips. The tube 20 is dipped 10–15 times.
5. A small needle (20 gauge) is inserted into the tube 20, just far enough to penetrate the outside wall but not enough to pierce through the bladder 30.
6. A small amount of warm water is pushed through the hole 23 into the bladder 30 to dissolve the gelatin. This is done several times until all of the gelatin mixture is pulled out of the bladder 30.
7. The needle hole is enlarged with a #11 blade scalpel to fit ⅛ inch pressure tubing 32.
8. The pressure tubing 32 is inserted into the hole 23 just flush with inner wall of the PVC tube.
9. Ultraviolet curable adhesive or polyurethane is deposited around the pressure tubing 32 and hole interface 23 and is allowed to cure with a UV light source or over time in room temperature (25 degrees Celsius), respectively.
10. The bladder 30 is then pressure tested with a Harvard Apparatus pressure transducer. It should be appreciated through industrial manufacturing techniques, this process can be expedited to a large degree. For example, the bladder(s) 30 may be formed directly into walls of tubing in a one-step extrusion process.

In the operation of the occluder device 16, the occluding mechanism 22 consists of a 3–6 inch piece of PVC tube 20 with a single bladder 30 molded onto the inner surface 24. The bladder 30 is 0.5 to 1.0 inches in length and is continuous along the inner radius of the tube 30. The bladder 30 is made of BFGoodrich Estanes that are US class 6 approved for implantation. These raw materials have been FDA approved for use in the intra-aortic balloon pump manufactured at Mansfield Scientific in Boston, Mass. A ⅛ inch pressure tubing 32 is ultraviolet-assist fixed to the outside of the PVC tube 20. This method employs the use of an adhesive, PVC Bonder from Loctite Corporation, that cures under exposure to ultraviolet light. An EFOS Ultracure 100 is the ultraviolet light source.

The occluder device 16 is placed over the outlet graft tubing 15 of the pump 14 which is arranged between the left atrium and the descending thoracic aorta. When the control means 18 senses that pump speed indicates malfunction, it actuates the bladder mechanism 22 to occlude the tubing 15. When inflated, the occluder device 16 prevents high pressure aortic blood from flowing back to the left atrium, LA, and into the lungs.

The occluder device 16 has been manually tested in vitro and found to cause near total occlusion of the tube graft 15 as shown by stoppage of gravity-driven flow. In this test, a Gore-tex® outlet graft was held with its long axis vertical. The occluder was placed around the graft and inflated to cause maximal occlusion at a pressure of approx 5–9 psi. The graft was then filled with tap water at the top end and the rate of leakage at the bottom end was qualitatively monitored.

In another in vitro test, the occluder 16 was positioned on the Gore-tex® outlet graft of the blood pump 14. The blood pump 14 was arranged in a mock circulatory loop. The occluder 16 was shown to reduce a flow of 5 L/min and a pressure of approximately 120 mmHg to 0.2 L/min (96% reduction in flow). The pressure on the downstream side of the occluder 16 was approximately 10 mmHg, which was the height of the mock loop fluid column reservoir. The pressure on the upstream side was approximately 180 mmHg. The occluder bladder pressure was 16 psi.) In acute in vivo testing in sheep, the occluder device 16 also caused total occlusion of pump graft tubing 15 in vivo at a flowrate of 3.5 L/min. and a mean arterial pressure (MAP) of 75 mmHg. The pump was running at the time to supply the pressure and flow. It was also shown to prevent retrograde flow at simulated pump motor failure (MAP 75 mmHg). This testing involved placing the occluder device 16 on the outlet flow tube 15 of the AB-180 in another acute implantation study with sheep. Pump motor failure was simulated by simply disabling power to the pump stator by switching the controller power off.

The occluder was placed externally over the outlet graft of two centrifugal blood pumps which were implanted in animals for chronic durations of 35 and 154 days. The blood pump was arranged and connected between the left atrium and the descending aorta to bypass the left ventricle. Pump motor failure occurred on POD 35 of the first implantation study. In order to test for prevention of reverse flow to allow time for intervention, the occlusion device 16 was manually activated and it prevented retrograde pump flow for a period of 90 minutes. In the 154 day study, the occluder was activated to prevent retrograde flow secondary to pump motor failure. It allowed only 0.2 L/min of reverse flow for 24 hours during complete motor failure. A partially automated circuit, including a small pneumatic bladder pump, a hysteresis pressure switch, a 12-Volt battery, and a pressure regulator were utilized to maintain adequate occlusion over the 24 hours.

It is estimated that 17,000–35,000 people could benefit from medium-term circulatory assist each year. The occluder device 16 could become an important safety feature for these circulatory assist devices.

The occluder device 16, as shown in FIGS. 7a–7c, can also be used as a device to apply certain impressions in surfaces of a molded object 70. This could be done by pouring mold material into the occluder, inflating the bladder 30, and deflating the bladder 30 when the mold material sets.

The occluder device 16 may be used in many additional applications. For instance, the occluder device 16 can be used by surgeons as a vascular occluder. Many times in cardiac surgery, surgeons utilize metal clamps to temporarily stop blood flow through certain vessels. The occluder device 16 would be more gentle on the vessel wall. The geometry of the occluder 16 may allow a more even distribution of stress on vessel walls when they are compressed. This is in contrast to hard metal clamps which may cause areas of significant stress concentration blood vessel walls. Less vessel wall stress could results in decreased chances for thrombus formation following surgery.

Figure 5:
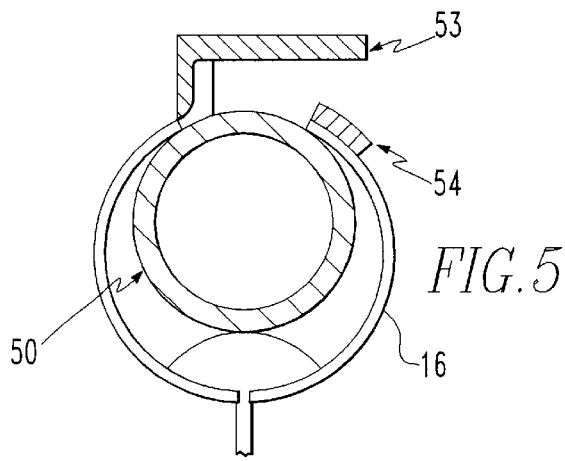
FIG. 5 is a schematic representation showing a C-shaped occluder device with Velcro® closures.

For example, as shown in FIG. 5, the occluder 16 could be placed across the descending aorta 50 during bypass surgery. The occluder device 16 can be made as a clam-shell design, with Velcro® portions 53, 54 holding the two halves together. It could be opened up, placed around the vessel 50, closed, and inflated to lamp. The Velcrom® 53, 54 provides great utility as it is extremely easy to fasten and can be reused.

Figure 6:
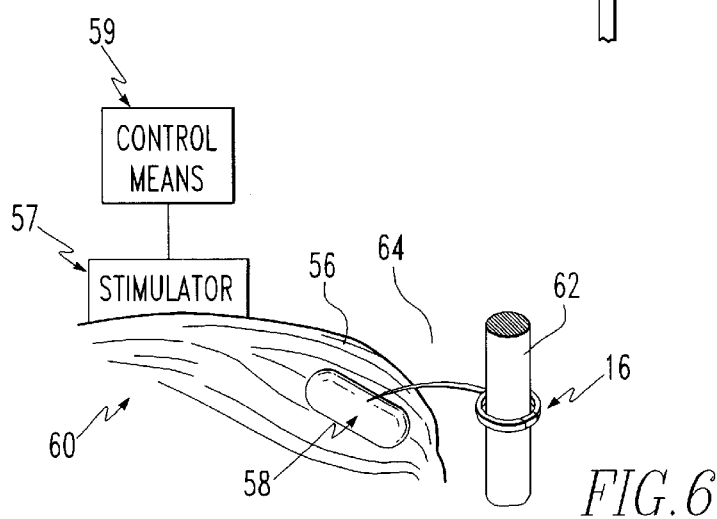
FIG. 6 is a schematic representation showing a system for controlling a body part of a person with a muscle of the person.

The occluder device 16 can also be activated with internal muscle forces. For instance, the anal sphincter works to push waste through and out of the rectum. It is a circular muscle that contracts radially (which creates a decreasing diameter). In persons whom the sphincter is compromised, the occluder device 16 could be used to work as a sphincter. It is possible to use muscle contraction to move fluid to and from the bladder 30 of the occluder 16 to simulate normal sphincter motion. As illustrated in FIG. 6, anatomically close muscles 56 could be connected to a muscle energy converter 58. One method would be to utilize the control means 16 to stimulate the gluteals to compress a fluid reservoir 58 connected to the bladder 30. The compression of the reservoir 58 by the muscle would cause the transfer of fluid to the bladder 30 and subsequent inflation. The reservoir 56 could be placed within the muscle belly of the gluteals 58. Stimulation of the gluteals by a commercially available muscle stimulator 57 would cause contraction of the muscle 56 and compression of the enclosed fluid reservoir 58. A typical muscle stimulator 57 which is electronically activated by control means 16 is model 10, available through Allegheny-Singer Research Institute of Pittsburgh, Pa. If the inflation of the bladders 30 was timed with a bowel movement, then this device 60 would operate similarly to a normal sphincter. The gluteals could be used as the source of muscle power for the device 60.

Thus, the present invention is also a system 60 for controlling an organ 62 of a person with a muscle 56. The system 60 comprises an occluder device 16 and a muscle energy convertor 64 having a reservoir 58 of fluid in fluidic communication with the bladder mechanism of the occluder device 16. Detailed information on muscle energy converters is disclosed in U.S. patent application Ser. No. 08/228,586 titled, "Muscle Energy Converter", filed on the same day as this application by Dennis Trumble, having attorney docket number AHS-5, incorporated by reference herein.

The occluder device 16 can also be used as a device to assist in peristalsis (normal muscular motion of esophagus during digestion). The occluder 16 could be placed around the esophagus and compressed periodically to aid in motion of food through the digestive tract. Some disorders exist where people have difficulty with normal muscular motion of the esophagus during digestion (peristalsis). The occluder 16 could be placed around the esophagus and it could have several bladders 30 along the length of the esophagus. The bladders 30 could be inflated in succession from the proximal to the distal end. This would serve to advance food toward the stomach. The actuation of this device could be controlled remotely or by muscles, as shown in FIG. 6.

Figure 9:
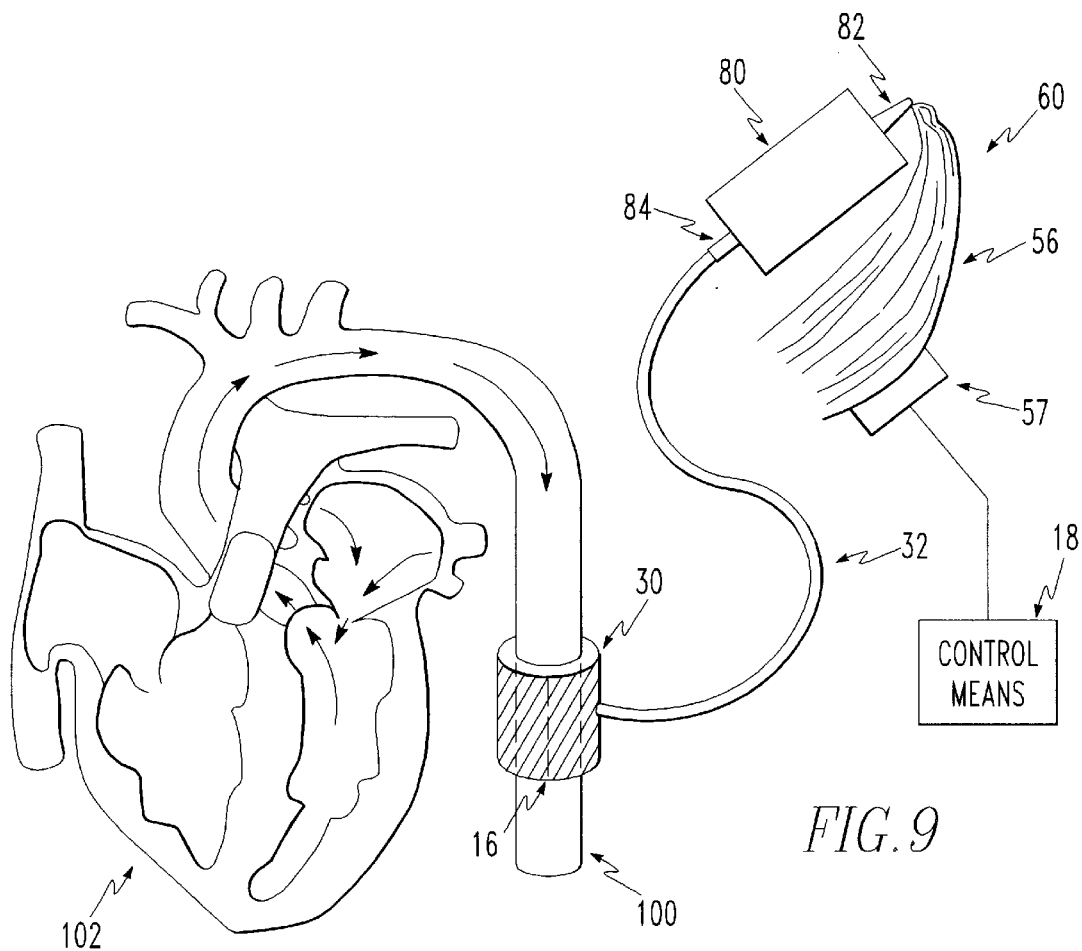
FIG. 9 is a schematic representation of the occluder device situated about the descending thoracic aorta and powered by a muscle for extra-aortic assist.

As shown in FIG. 9, the occluder device 16 can be also used as a device to externally compress the aorta 100 during diastole to assist in moving blood. This is similar to an intraaortic balloon pump except the occluder device would not contact the blood. This application, known as extra-aortic compression, has not been used before with an external inflatable occluder. However, some researchers have wrapped skeletal muscle around the aorta 100 to compress it during muscular stimulation. This is known as aortomyoplasty. It is similar to the cardiomyoplasty procedure at Allegheny General Hospital in Pittsburgh, Pa., where muscle is wrapped around the heart 102 to cause direct ventricular compression. The use of the occluder device 16 to do this would be considerable simpler and have tremendous utility. The occluder device 16 would accomplish the same task as the intra-aortic balloon pump, except externally without blood contact.

The use of the occluder device in conjunction with a muscle energy converter, system 60, as stated could be a tremendous tool in circulatory assist (incorporated by reference-"The Rationale for Skeletal-Muscle-Powered Counterpulsation Devices: An Overview", Journal of Cardiac Surgery, Vol. 1, No. 4, 1986, pp. 385–392). Present devices that contact blood are limited in use due to issues of infection, thromboembolic complications, thrombus, hemorrhage, mechanical wear, etc. The use of the system 60 for an extra-aortic assist device, and having the occluder 16 and muscle energy converter 80, eliminates the chance of many of these complications since the system 60 is non-blood contacting. In addition, people awaiting heart transplantation can be aided in the meantime, or it may be possible to eliminate the need for a patient to require a heart transplant altogether by using one of these devices chronically. For instance, this system 60 which should perform similarly to the intraaortic balloon pump, could take over approximately 20% of the heart's function on a long-term basis (up to several years). This could allow a patient with mild to medium heart failure to lead a much more normal life. In order to maintain synchrony, an ECG monitor 93 can be used and connected to the control means 18. One major concern with this type of system 60 is its effect on the wall of the aorta after continual cyclic compression which is timed with the patient's ECG. However, studies conducted at Allegheny General Hospital conducted by Dr. Robert R. Lazzara have shown that the skeletal muscle wrapped around the aorta has essentially no detrimental effect on the aorta wall following several months of cyclic compression based on histology and pathology reports.

As shown in FIGS. 8a and 8b, the occluder device 16 can also be used as a device placed around other organs 62, such as the gall bladder to assist in the transport of bile out of the gall bladder. Again, this could be accomplished by simply inflating the bladder 30. This application may require various changes in geometry of the occluder 16 to accommodate the organ. The gall bladder, which is roughly an ellipse, could be surrounded by an occluder device 16 (with a similar shape) that could compress it and force bile through the bladder and out the bile duct. The occluder device 16, with alterations to shape it more closely to the gall bladder, may serve to accomplish this. The manufacturing technique would be the same as described above except the tube would be of an elliptical shape.

As shown in FIG. 8c, the occluder device 16 can also be used as a dietary control device. Patients suffering dietary ailments sometimes resort to having portions of their stomach stapled to decrease the overall inner surface area of the stomach. This causes a decreased appetite because the stomach stretch receptors in portions of the stomach that are compressed undergo larger displacement than they would normally since the stomach volume has been reduced. They then send a stronger signal to the brain that results in an enhanced feeling of fullness. The occluder 16 could be modified and enlarged and placed around the stomach organ. By inflating the bladders 30 of the occluder 16, the stomach could be compressed and its volume decreased. This would accomplish the same task as stapling but would be remotely adjustable. That is, the amount of occlusion or decrease in stomach volume could be adjusted remotely by applying more or less bladder pressure based on an individuals dietary requirements.

As shown in FIG. 8c, the occluder frame 106 could be modified to completely surround the stomach with vents such that the entire volume of the stomach is constrained. Inflation of the bladder 30 would decrease stomach volume.

Placement of the occluder 16 around the stomach would require surgery. After the patient's diet was under control, the occluder 16 could be slowly released and the device explanted.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. A method of forming an occluder comprising the steps of:

disposing a mask material on an inner surface of a tube;

applying a bladder mate rial to the inner surface over the mask material; and providing a hole through the tube under the mask material for inflating the bladder material.

2. A method as described in claim 1 wherein after the providing step, there is the step of removing the mask material through the hole.

3. A method as described in claim 2 wherein the removing step includes the step of circulating a heated fluid through the hole to dissolve the mask material.

4. A method as described in claim 3 wherein after the circulating step, there is the step of attaching a tube to the hole.

5. A method as described in claim 4 wherein the disposing step includes the step of placing gelatin material on the inner surface.

6. A method as described in claim 5 wherein the applying step includes the step of pouring bladder material into the tube.

7. A method as described in claim 6 wherein after the pouring step, there is the step of spinning the tube to create a uniform coating.

* * * * *